United States Patent [19]
Wolf et al.

[11] Patent Number: 5,370,534
[45] Date of Patent: * Dec. 6, 1994

[54] WATER PURIFICATION SYSTEM FOR DENTAL INSTRUMENT

[75] Inventors: Leo H. Wolf; Mark F. Wolf, both of River Falls, Wis.

[73] Assignee: Time Motion Systems Company, River Falls, Wis.

[ * ] Notice: The portion of the term of this patent subsequent to Jul. 27, 2010 has been disclaimed.

[21] Appl. No.: 97,162

[22] Filed: Jul. 23, 1993

Related U.S. Application Data

[63] Continuation-in-part of Ser. No. 973,454, Nov. 9, 1992, Pat. No. 5,230,624.

[51] Int. Cl.$^5$ .............................................. A61C 1/10
[52] U.S. Cl. ........................................ 433/80; 433/82
[58] Field of Search .................. 433/80, 81, 82, 84, 433/85, 86, 87, 88

[56] References Cited

U.S. PATENT DOCUMENTS

| | | | |
|---|---|---|---|
| 3,593,423 | 7/1971 | Jones et al. | 433/80 |
| 3,698,088 | 10/1972 | Austin, Jr. | 433/80 |
| 3,772,189 | 11/1973 | Kreusch et al. | 210/753 |
| 3,817,860 | 6/1974 | Lambert et al. | 210/753 |
| 3,923,665 | 12/1975 | Lambert et al. | 210/501 |
| 4,059,522 | 11/1977 | Polley et al. | 210/753 |
| 4,190,529 | 2/1980 | Hatch | 210/753 |
| 4,238,477 | 12/1980 | Lambert et al. | 424/79 |
| 4,741,697 | 5/1988 | Herbison | 433/80 |
| 4,743,229 | 5/1988 | Chu | 604/82 |
| 4,888,118 | 12/1989 | Barnes et al. | 210/753 |
| 4,950,159 | 8/1990 | Hansen | 433/80 |
| 4,961,698 | 10/1990 | Vlock | 433/88 |
| 4,973,247 | 11/1990 | Varnes et al. | 433/82 |
| 4,978,297 | 12/1990 | Vlock | 433/88 |
| 4,999,190 | 3/1991 | Fina et al. | 424/79 |
| 5,024,600 | 6/1991 | Kline | 433/82 |
| 5,026,359 | 6/1991 | Burroughs | 210/501 |
| 5,110,479 | 5/1992 | Frommer et al. | 210/662 |
| 5,208,933 | 5/1993 | Lustig et al. | 15/22.1 |

OTHER PUBLICATIONS

"MCV Resin: Iodination Treatment Based on Space Technology", *Water Conditioning & Purification*, Mar. 1992, pp. 34, 38–40.

*Primary Examiner*—John J. Wilson
*Attorney, Agent, or Firm*—Burd, Bartz & Gutenkauf

[57] ABSTRACT

A dual cartridge system for purifying water supplied to a dental unit and dynamic dental instrument has two disposable elements, each having an iodinated anionic exchange resin containing a continuous fixed-rate release iodinated resin $I_{(n)}$. Iodine is released from the resin at a specified and consistent rate as water passes through the resin to maintain dental water purity. One cartridge is located in the dental unit water supply tubing. A second cartridge is located in the water supply tubing adjacent the connection to the water supply system. The iodinated biocidal resin in each cartridge neutralizes and kills disease-causing bacteria, virus, protozoa, aspirated oral flora and prevents microbial backgrowth to eliminate cross-infection between dental patients.

25 Claims, 5 Drawing Sheets

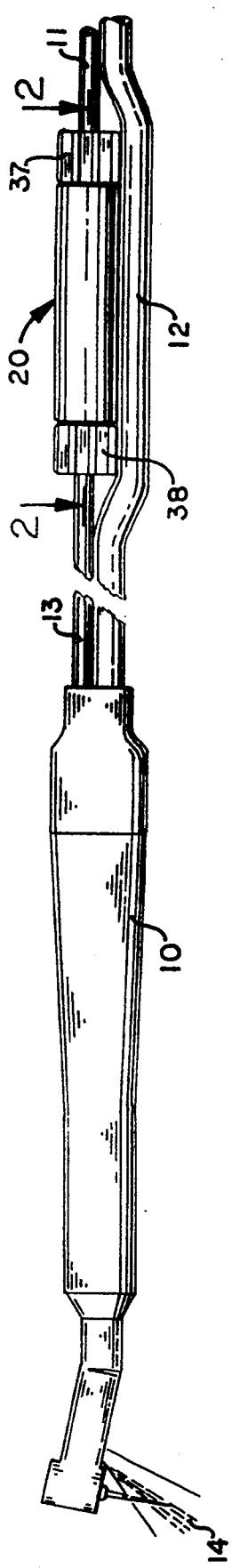
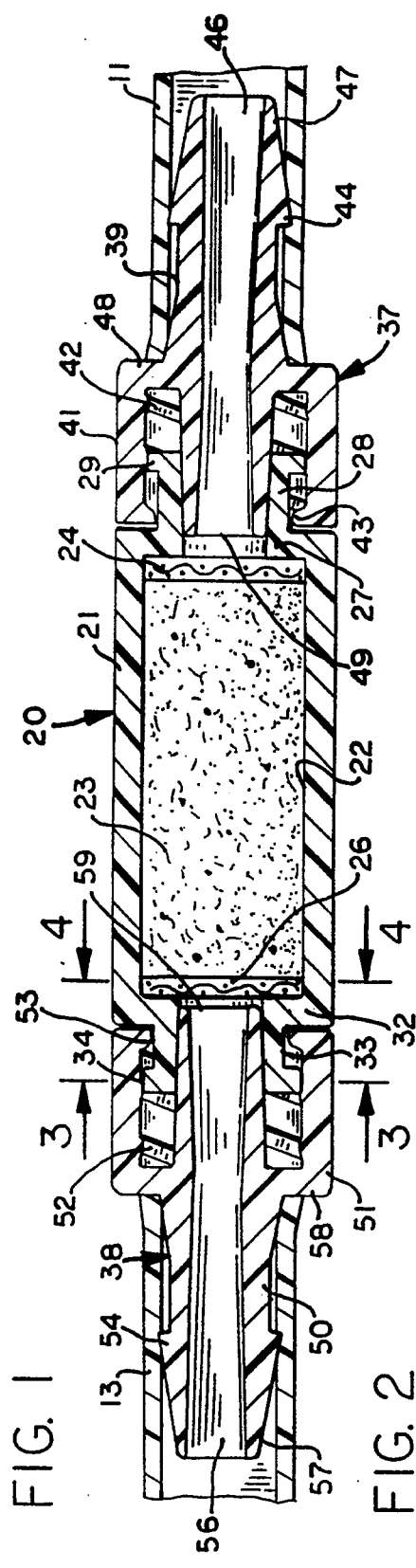
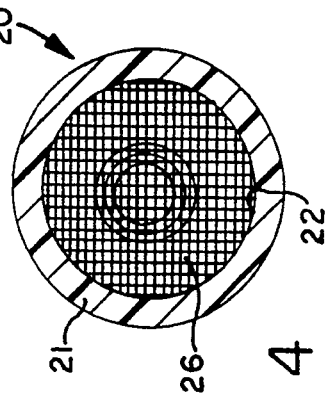
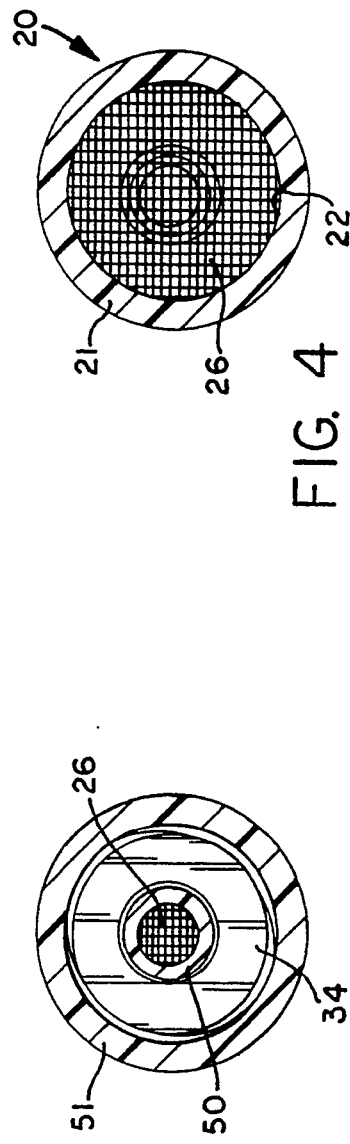
FIG. 1
FIG. 2
FIG. 4
FIG. 3

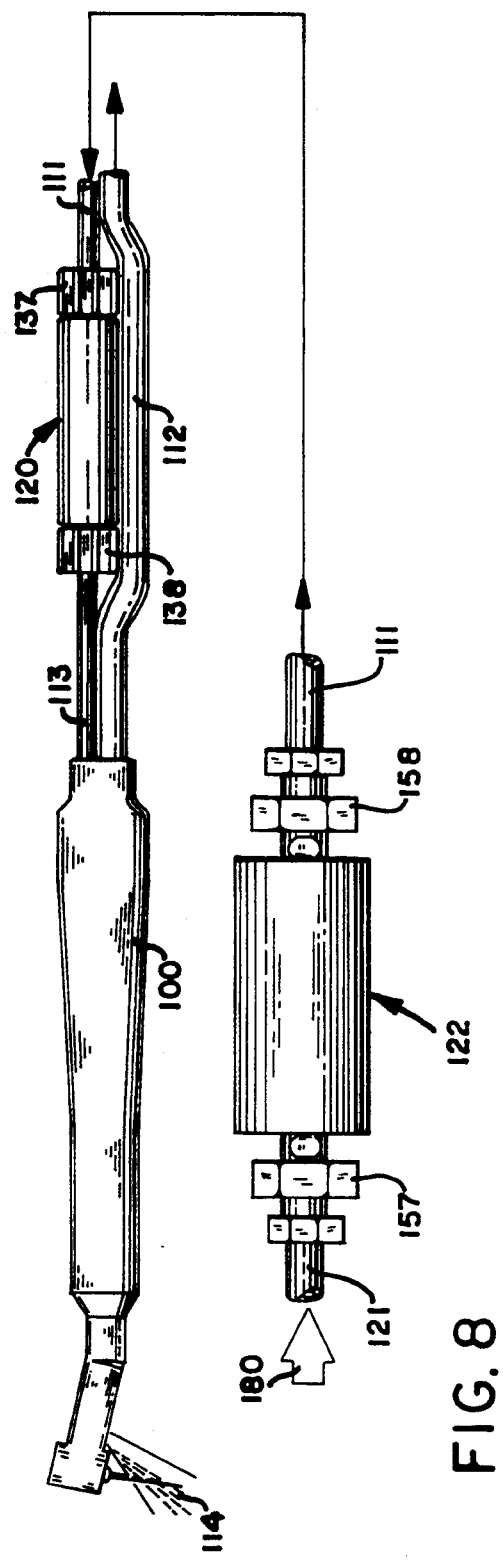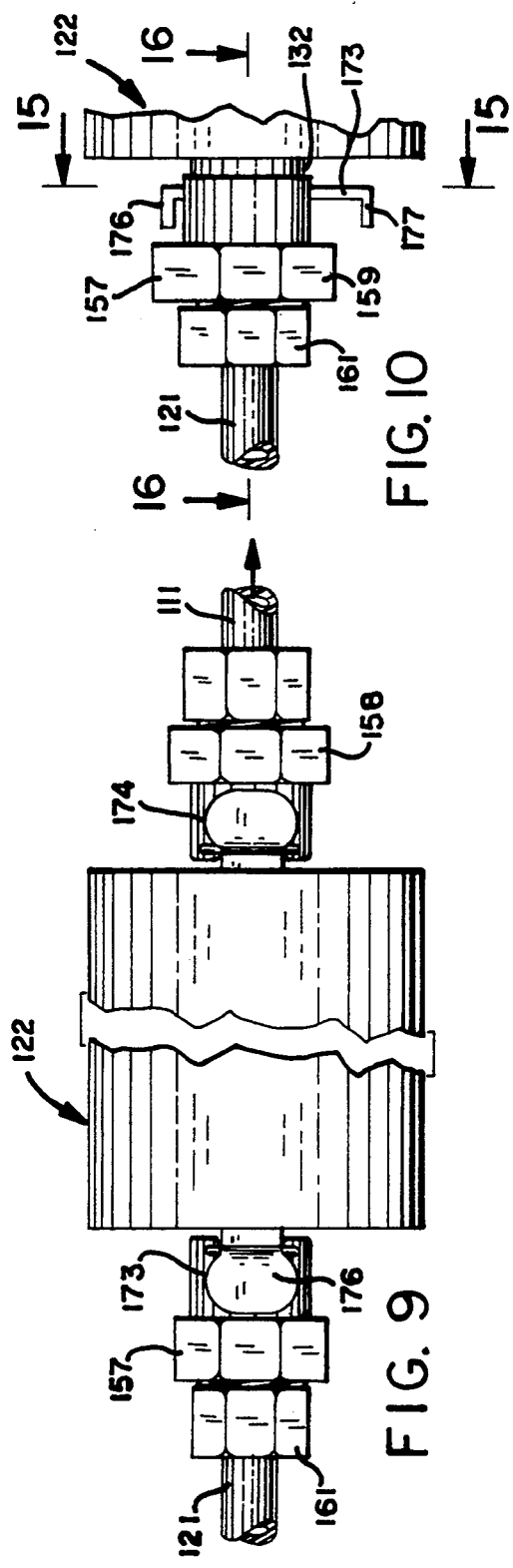

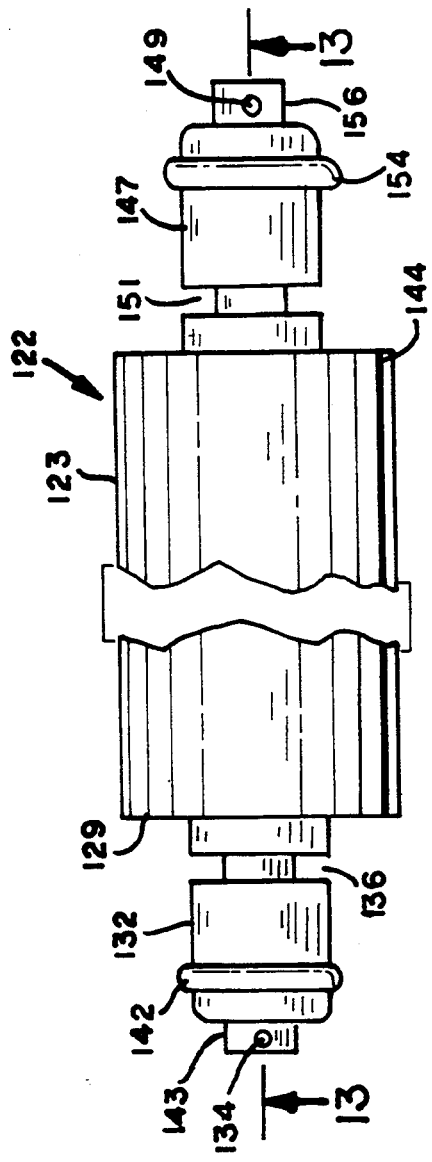
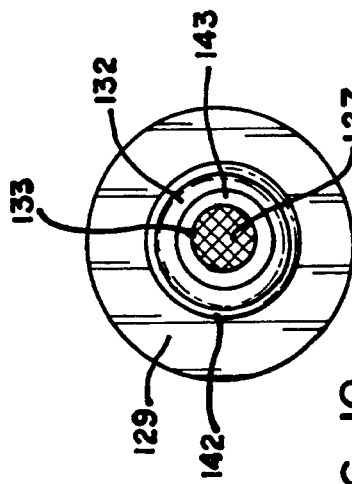
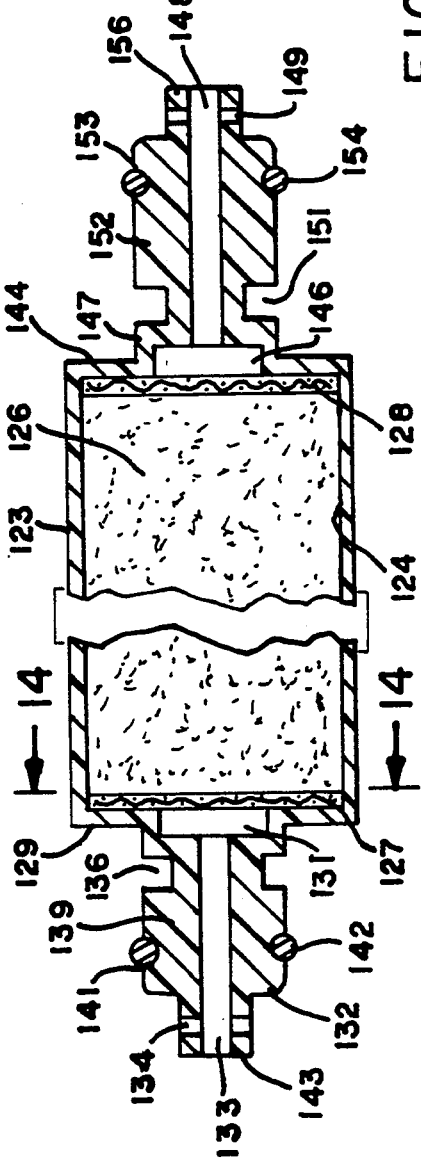
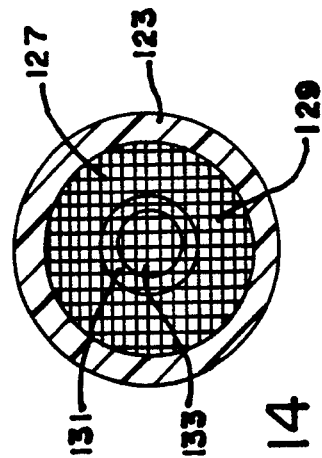

WATER PURIFICATION SYSTEM FOR DENTAL INSTRUMENT

CROSS REFERENCE TO RELATED APPLICATION

This application is a continuation-in-part of U.S. application Ser. No. 07/973,454 filed Nov. 9, 1992, now U.S. Pat. No. 5,230,624.

FIELD OF THE INVENTION

The invention relates to modern dental units containing a water supply system that provides coolant and rinse water to the high-speed dental handpiece, ultrasonic scaler and air/water syringe.

BACKGROUND OF THE INVENTION

All modern dental units have a water supply that provides coolant and rinse water to the dynamic dental instruments including the high-speed handpiece, air/water syringe and ultrasonic scaler. This water supply is connected to a domestic water system. Microbiological studies of this water supply revealed that the water is contaminated by water organisms and oral flora. These organisms have been found to be massive in number and some identified as pathogenic. Dental researchists have stated that this contamination could cause infection in immuno-suppressed patients, and cross infection may occur between dental patients.

Clinical tests show that oral flora is aspirated from a patient's oral cavity into the dental unit water lumens through the dynamic dental instruments. This revelation has prompted the Centers of Disease Control to recommend a 20 to 30 second purge of these instruments between each patient appointment. The American Dental Association and The American National Standards Institute developed Specification Number 47, dated Apr. 12, 1984, as the manufacturing criterion for dental unit manufacturers. This specification requires that a means be incorporated in the dental unit to prevent water from being drawn back beyond the point of the dental instrument connection. These are attempts to improve the quality of water used for dental treatment. However, continuing research indicates that neither has significantly reduced contamination.

Medical studies have determined that disease incubation periods vary. Because of this variance it is difficult to make accurate assessments as to the time and place of infection. Dental treatment is frequently subgingival and invasive of the mucosa therefore providing a direct access to the vascular system. It is therefore prudent to use microbiologically pure water for cooling and rinsing during dental treatment in lieu of water considered by public health standards to be polluted and nonpotable.

SUMMARY OF THE INVENTION

The invention is directed to a water purification apparatus used to maintain dental unit water quality.

The apparatus incorporates a quick connect cartridge in the water lumen of a dynamic dental instrument tubing. The cartridge contains a continuous, fix-rate release iodinated resin $I_{(n)}$. This biocidal resin neutralizes and kills disease causing bacteria, virus and protozoa as water flows through the cartridge. The resin elutes a residual iodine at a constant predetermined rate to maintain a purified water condition within the dental unit water supply. A residual iodine is released from the resin as the water passes through the resin and remains in the water between the cartridge and the dynamic instrument. As the instrument is used aspirated oral flora are killed by the residual iodine and are prevented from traveling back beyond the cartridge at point of use. This maintains a microbiologically pure water condition by preventing back growth of bacteria thus reducing cross infection potential and preventing disease transmission by way of the dental unit water. Quick releasable lock structures are used to connect opposite ends of the cartridge to the water carrying tubes. At the beginning of each work day, the cartridge is changed on each water lumen of the dental unit to maintain microbiologically pure water conditions for that work day period.

DESCRIPTION OF DRAWING

FIG. 1 is a side elevational view of a dental handpiece attached to a water supply line including a water disinfectant element or cartridge;

FIG. 2 is an enlarged sectional view taken along the line 2—2 of FIG. 1;

FIG. 3 is a sectional view taken along the line 3—3 of FIG. 2;

FIG. 4 is a sectional view taken along the line 4—4 of FIG. 2;

FIG. 8 is a side elevational view of a dental handpiece attached to a water supply line equipped with a first water disinfectant cartridge and a water source line having a second water disinfectant cartridge;

FIG. 9 is an enlarged fragmentary top view of the second water disinfectant cartridge and releasable connectors attached thereto;

FIG. 10 is an enlarged side view of one end of the second water disinfectant cartridge and releasable connector attached thereto;

FIG. 11 is a fragmentary top side elevational view of the second disinfectant cartridge;

FIG. 12 is an end view of FIG. 11;

FIG. 13 is a fragmentary sectional view taken along the line 13—13 of FIG. 11;

FIG. 14 is a sectional view taken along the line 14—14 of FIG. 13;

DESCRIPTION OF PREFERRED EMBODIMENT

Figure 6:
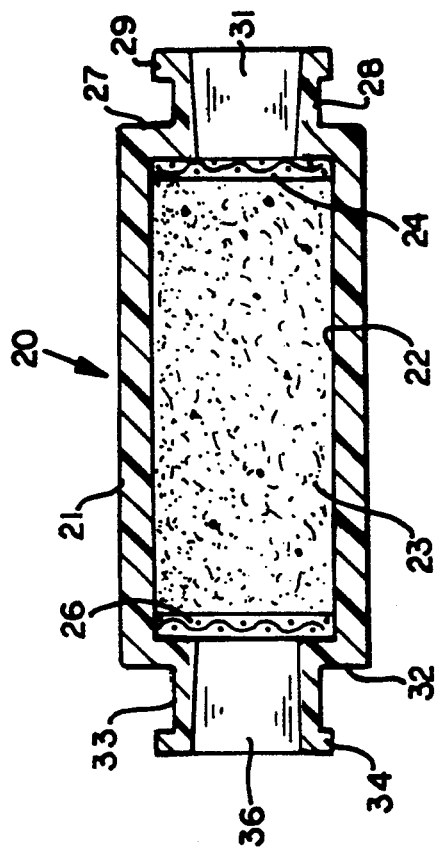
FIG. 6 is a top plan view of the cartridge.

Referring to FIG. 1, there is shown a dental instrument 10 having a water intake tube 13 and an air tube 12. Dental instrument 10 is shown as a dental handpiece. Dental handpiece 10 can also be an air/water syringe, ultrasonic scaler or other dynamic dental instrument. A water supply tube 11 leading to dental handpiece 10 includes a water purification and disinfectant element or cartridge of the invention, indicated generally at 20. Cartridge 20 is located in the water line between water tubes 11 and 13. Releasable quick connect lock structures or fittings 37 and 38 mounted on the ends of tubes 11 and 13 are used to connect opposite ends of cartridge 20 to tubes 11, 13. Cartridge 20 cleans and disinfects water passing through the cartridge and supplies a residual disinfectant to the water that remains in the water as it moves between cartridge 20 and dental handpiece 10. The residual disinfectant of the cartridge 20 neutralizes water contaminants that may be drawn back into the water system for dental handpiece 10.

Referring to FIGS. 2 to 7, cartridge 20 is a generally cylindrical member having a housing 21 surrounding a tubular chamber 22. Cartridge 20 is manufactured to retrofit the tubing of modern dental units. Cartridge chamber 22 contains a resin and/or filter material 23, as seen in FIGS. 2 and 6, that functions to purify and release residual disinfectant into water passing through cartridge 20 to kill or prevent cell reproduction of water contaminants. This ensures that water spray 14 discharged from handpiece 10 is in a pure condition and contains a disinfectant thereby reducing the potential of cross infection between dental patients and preventing disease transmission via the dental instrument water system.

For example, disinfectant material 23 can be a purification resin containing the polyiodide, $I_5$ as disclosed by Lambert and Fina in U.S. Pat. No. 4,238,477, and Fina, Lambert and Bridges in U.S. Pat. No. 4,999,190. As water flows through cartridge 20, the iodinated resin neutralizes and extinguishes disease causing bacteria, virus, protozoa and other microorganisms that may be present in the water by means of a continuous release of iodine at a predetermined level. The resin can also be an iodinated anionic exchange resin manufactured and sold under the trademark MCV by MCV Technologies International, Inc., of Belleville, Ill. This resin releases a specific and consistent amount of iodine which kills all microbial contaminants including bacteria, viruses and cysts or preventing cell reproduction rendering the contaminant harmless. The resin releases residual iodine into the water as the water passes through cartridge 20 and prevents back growth of bacteria aspirated into the tubing. The iodine remains as a residual in the water line between cartridge 20 and dental handpiece 10. Aspirated oral flora and other contaminants are destroyed by the residual iodine in the water and are prevented from traveling back beyond the cartridge 20. This maintains a microbiologically pure water condition and prevents disease transmission through the handpiece water system with subsequent use of handpiece 10. Other types of resins and neutralizing agents can be used as disinfectant material 23 for cartridge 20.

Figure 5:
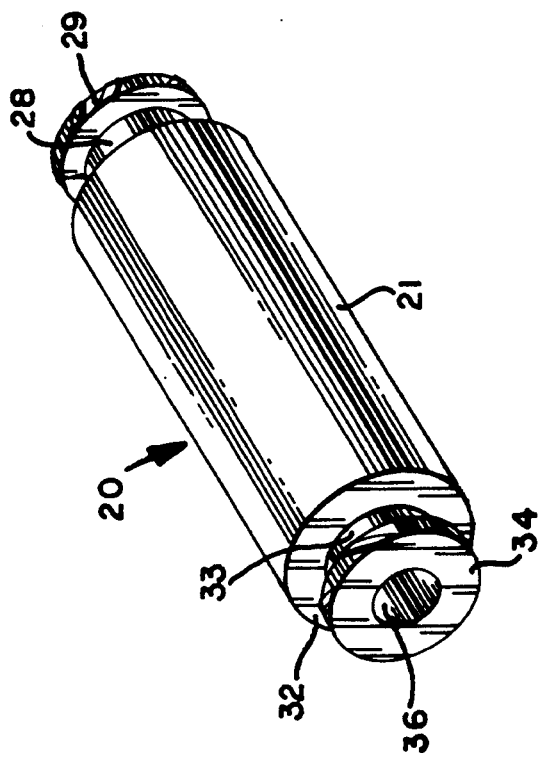
FIG. 5 is a perspective view of the cartridge.
Figure 7:
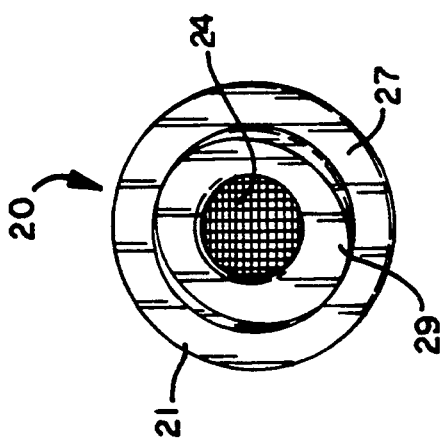
FIG. 7 is an end view of the cartridge, the opposite end being a mirror image thereof.

Disinfectant material 23 is held within chamber 22 by a pair of transverse filter members 24 and 26 located at opposite ends of chamber 22. Filter members 24 and 26 have a circular shape with a plurality of relatively small openings in the form of a filter material, as seen in FIGS. 4 and 7, to allow passage of water through cartridge 20 while retaining disinfectant material 23 within chamber 22. Other shapes and opening patterns may be used to construct filter members 24 and 26. Filter members 24 and 26 have a tight fit relationship with the inside surface of housing 21. Housing 21 has end walls 27 and 32 located adjacent the outer peripheral surfaces of filter members 24, 26, respectively. End wall 27 has a centrally located passage 31 surrounded by an outwardly extended tubular collar 28. The diameter of passage 31 is less than the diameter of filter member 24. Water enters cartridge 20 through passage 31 from water supply tube 11 and flows through filter member 24 and disinfectant material 23 for purification. The outer end of collar 28 has an annular flange 29 with a threaded outer surface, as shown in FIG. 5, that cooperates with a threaded fitting 37 to releasably connect end 27 of cartridge 20 to water supply tube 11.

Similarly, end wall 32 of cartridge 20 has a central passage 36 surrounded by an outwardly extended tubular collar 33. The diameter of filter member 26 is greater than the diameter of passage 33. Water enters cartridge 20 through passage 31 from water supply tube 11, flows through filter member 24 and/or disinfectant filter material 23 and then out filter member 26 and passage 36 into water intake tube 13 connected to dental instrument 10. Water flowing through passage 36 is in a microbiologically purified condition and contains a residual disinfectant that remains in water spray 14 to destroy aspirated oral flora and other contaminants that may be drawn back into the dental unit water system. The outer end of collar 33 has an annular flange 34 with a threaded outer surface, as shown in FIG. 5, that cooperates with a second threaded fitting 38 to releasably connect cartridge 20 with water intake tube 13.

Ends 27 and 32 of cartridge 20 are substantially the same and are interchangeable whereby either end 27, 32 of cartridge 20 can be connected to water supply tube 11 or water intake tube 13 and vice versa. For example, when end 32 is attached to water supply tube 11 and end 27 is attached to water intake tube 13, water flows into cartridge 20 through passage 36 and moves out of the cartridge through passage 31. This eliminates the necessity of an alignment procedure during installation of cartridge 20 in instrument 10.

Referring to FIG. 2, fitting 37 has a generally tubular body 39 having an internal passage 46. A ring 41 surrounding inner end 49 of body 39 has an inwardly directed wall 48 attached to body 39. Collar 28 of cartridge 20 telescopes into ring 41 and surrounds inner end 49 of body 39. The inside surface of ring 41 has threads 42 that accommodate threads on the outer surface of flange 29 to releasably hold fitting 37 on cartridge 20. The outer end of ring 41 has an inwardly projecting lip 43 that engages the outer surface of collar 28. The top surface of lip 43 is located adjacent end wall 27 of cartridge 20 when the outer threaded surface of flange 29 is tightly threaded on threads 42 of fitting 37. Inner end 49 of body 39 is located in passage 31. End 49 is slightly tapered to facilitate insertion thereof into passage 31.

As shown in FIG. 2, the outer diameter of body 39 increases to a diameter that is substantially the same as the diameter of passage 31. This prevents water from leaking between water supply line 11 and cartridge 20. Outer end 47 of body 39 is inserted into the passage of water supply tube 11. End 47 has a tapered outer surface to facilitate insertion of end 47 into the passage of water supply tube 11. Fitting 37 has a foot 44 located adjacent end 47 to prevent fitting 37 from inadvertently slipping out of water supply tube 11. The outer surface of body 39 diverges outwardly to form foot 44. The diameter of foot 44 is slightly larger than the diameter of the passage in water supply tube 11 thereby expanding water supply tube 11 when body 39 is located in the tube passage to provide holding action. The middle portion of body 39 also diverges outwardly to an increased diameter, as seen in FIG. 2, to provide additional holding action. The end of water supply tube 11 engages wall 48 when fitting 37 is fully inserted into the passage of water supply tube 11.

Fitting 38 has substantially the same structure as fitting 37. Fitting 38 has a tubular body 50 with an internal passage 56. A ring 51 surrounds inner end 59 of body 50.

Ring 51 has an inwardly directed wall 58 secured to body 50. Collar 33 of cartridge 20 telescopes into ring 51 and surrounds inner end 59 of body 50. The inside surface of ring 51 has a plurality of threads 52 that accommodate threads on the outer surface of flange 34 to releasably hold fitting 38 on cartridge 20. Ring 51 has a lip 53 that engages the outer surface of collar 33. The top surface of lip 53 is located adjacent end wall 32 of cartridge 20 when the outer threaded surface of flange 34 is tightly threaded on threads 52 of fitting 38. Ends 57 and 59 of body 50 have tapered outer surfaces to facilitate insertion thereof into the passage of water intake tube 13 and cartridge passage 36, respectively. Fitting 38 has a foot 54 located adjacent end 57 that engages the lumen of water intake tube 13 to prevent fitting 38 from inadvertently slipping out of water intake tube 13, as seen in FIG. 2.

In use, cartridge 20 is inserted between water supply tube 11 and water intake tube 13 in the water line leading to dental handpiece 10 or other dynamic dental instrument. Fittings 37 and 38 mounted on the ends of tubes 11 and 13 releasably lock opposite ends of cartridge 20 onto the ends of tubes 11 and 13. Outer threaded surfaces of cartridge flanges 29 and 34 engage threaded inner surfaces 42 and 52 of fittings 37 and 38 to releasably hold the cartridge on water tubes 11 and 13. Cartridge 20 contains disinfectant material 23 that purifies and adds residual disinfectant to water supplied to dental handpiece 10. The residual disinfectant destroys contaminants and disease causing microorganisms when they are drawn back into the water line. This maintains a microbiologically pure water system for dental handpiece 10 preventing cross infection between dental patients. Filter members 24 and 26 contained within chamber 22 of cartridge 20 prevent passage of disinfectant material 23 from cartridge 20 and in addition filter particulate.

At the beginning of each work day cartridge 20 is changed. The threaded surfaces of cartridge flanges 29 and 34 and threaded fitting surfaces 42 and 52 are separated to quickly remove cartridge 20 from fittings 37 and 38 secured to tubes 11 and 13. Cartridge 20 is discarded and then the opposite ends of a new cartridge can be quickly connected to fittings 37 and 38. This maintains a microbiologically pure water condition and prevents cross-contamination during subsequent use of handpiece 10.

Referring to FIGS. 8 to 16, there is shown a modified dental instrument 100 having a water intake tube 113 and an air tube 112. Dental instrument 100 is substantially the same as dental handpiece 10 shown in FIG. 1 and described above. Dental instrument 100 can also be an air/water syringe or ultrasonic scaler or other dynamic dental instrument. A water supply tube 111 leading to dental instrument 100 is releasably coupled to a first water disinfectant cartridge of the invention indicated generally at 120 and a second water disinfectant cartridge of the invention indicated generally at 122. Cartridge 120 is identical to cartridge 20 described above. Cartridges 120 and 122 clean and disinfect water passing through cartridges 120 and 122 and supply a residual disinfectant to the water. The residual disinfectant remains in the water as it moves through tubes 11 and 113 into dental instrument 100. The residual disinfectant neutralizes water contaminants that may be drawn back into the water system for dental instrument 100 and neutralizes water contaminants originating from the domestic or community water supply system whereby water spray 114 discharged from the dental instrument is in a pure condition and contains a disinfectant. This reduces the potential of cross infection between dental patients and prevents disease transmission via the dental instrument water system or the domestic water supply system.

Referring to FIG. 8, cartridge 120 is located in the water line between water tubes 111 and 113. Releasable quick connect fittings 137 and 138 mounted on the ends of tubes 111 and 113 are used to connect opposite ends of cartridge 120 to tubes 111 and 113.

A second water disinfectant cartridge 122 is located in the water line between water supply tube 111 and a water source tube 121. Cartridge 122 is installed in the dental instrument water system at the point of connection to a self contained water system or a domestic water supply system, which reinforces and or replaces a domestic or community purification system. Cartridge 122 is used at geographic locations where a domestic or community water purification system does not exist or is inadequate. Releasable connectors 157 and 158 mounted on the ends of tubes 111 and 121 connect opposite ends of cartridge 122 to tubes 111 and 121.

Cartridge 120 is substantially the same as cartridge 20 shown in FIGS. 1 to 7 and described above. Cartridge 120 contains a resin or disinfectant material (not shown) substantially similar to resin 23 of cartridge 20 that functions to filter, purify and release residual disinfectant into water passing through the cartridge to kill or prevent cell reproduction of water contaminants. The cartridge 120 is used to provide microbiologically pure water to the dental unit and to prevent back contamination to the water supply system. Fittings 137 and 138 are identical to fittings 37 and 38 shown in FIG. 2. The ends of cartridge 120 are threaded into fittings 137 and 138 to releasably hold the fittings 137 and 138 on cartridge 120. The outer end of fitting 137 is inserted into the passage of water supply tube 111. The outer end of fitting 138 is inserted into the passage of water intake tube 113. Fittings 137 and 138 releasably lock opposite ends of cartridge 120 onto the ends of tubes 111 and 113.

Referring to FIGS. 9 to 16, cartridge 122 is a generally cylindrical member having a housing 123 surrounding a tubular chamber 124. The chamber 124 contains a disinfectant material 126 and/or filter material 128, as seen in FIG. 13. Disinfectant material 126 is the same as the disinfectant material contained in cartridge 120 and disinfectant material 23 in cartridge 20. Disinfectant material 126 purifies water from community water supply line 121 and releases residual disinfectant into water passing through cartridge 122 to kill or eliminate cell reproduction of water contaminants and tubing biofilm. This reduces the potential or cross infection between dental patients and prevents disease transmission via the dental instrument water system or the domestic water supply system.

Disinfectant material 126 and the filter material 128 contained in cartridge 120 can be resins containing the polyiodide, $I_5$, as disclosed in U.S. Pat. Nos. 4,238,477 and 4,999,190. As water flows through cartridges 120 and 122 a continuous fix-rate release of iodine at a predetermined level from the iodinated resins neutralizes and extinguishes disease causing agents, such as bacteria, virus, protozoa and other microorganisms that may be present in the dental instrument water system or the domestic water supply system. The resins can also be iodinated anionic exchange resins manufactured and sold under the trademark MCV by MCV Technologies International, Inc., of Belleville, Ill. These resins release a specified and consistent amount of iodine which kills all microbial contaminants, such as bacteria, viruses and cysts in the dental instrument water system and the domestic water supply system or prevents reproduction of cells rendering the contaminants harmless. The resins also release iodine into the water as it passes through cartridges 120 and 122. The iodine remains as a residual in the water line between cartridge 122 and cartridge 120 and between cartridge 120 and dental instrument 100. Aspirated oral flora and other contaminants in the dental instrument water or the domestic water supply systems are destroyed by the residual iodine remaining in the water. This maintains a microbiologically pure water condition and purifies water supplied from the domestic water supply system. Other types of resins and neutralizing agents can be used as the filter material for cartridges 120 and 122.

Disinfectant material 126 is held in chamber 124 with filters 127 and 128 located at opposite ends of chamber 124. Filters 127 and 128 allow passage of water through cartridge 122 while retaining disinfectant material 126 within chamber 124. Filters 127 and 128 fit tightly into housing 123 adjacent end walls 129 and 144 of the housing, respectively. End wall 129 has a centrally located passage 131 surrounded by outwardly extended collar 132 having a generally tubular body 139. As shown in FIG. 13, passage 131 has a reduced diameter outer section 133 in communication with end openings or ports 134. Water enters cartridge 122 through ports 134 from water source tube 121 and flows through passage 131 through filter 127 and disinfectant material 126 for purification. The inner end of collar body 139 has a channel-shaped annular groove 136 that cooperates with a fastener or lever 173 of connector 157 to releasably connect end 129 of cartridge 122 to water source tube 121. A second annular groove 141 in body 139 spaced outwardly from groove 136 accommodates an O-ring or seal 142. The seal 142 prevents water leakage from the flow path 167 of connector 157 when connector 157 is coupled to collar 132. Outer end 143 of body 139 has a reduced outer diameter whereby end 143 can be inserted into inner chamber 163 of connector 157, as shown in FIG. 16.

Referring to FIG. 13, end wall 144 of cartridge 122 has a central passage 146 surrounded by an outwardly directed collar 147 having a generally tubular body 152. Passage 146 has a reduced diameter outer section 148 that communicates with ports 149. Water flows through passage 146 and moves out of cartridge 122 through ports 149 into tube 111 connected to cartridge 120. Water flowing through ports 149 into tube 111 is in a microbiologically purified condition and contains a residual disinfectant that remains in the water to kill or prevent water contaminant cell reproduction. The cartridge 122 is used to provide microbiologically pure water to the dental unit and to prevent back contamination to the water supply system. In this manner cartridge 122 reinforces existing purification systems or takes the place of a domestic or community purification system at geographic locations where such a purification system is non-existent. The inner end of body 152 has an annular groove 151 that accommodates and cooperates with a lever 174 of connector 158 to quickly releasably connect and disconnect cartridge end 144 to and from the end of water supply tube 111. An O-ring seal 154 located in a a second annular groove 153 in body 152 prevents water leakage from connector 158 when connector 158 is fitted on collar 147. The outer end of collar body 152 has a reduced diameter so that end 156 can be moved into the inner chamber of connector 158.

Ends 129 and 144 of cartridge 122 are identical and interchangeable whereby either end 129, 144 can be coupled to water supply tube 111 or water source tube 121 and vice versa. Thus, end 144 can be releasably attached to connector 157 to join end 144 to water source tube 121 and end 129 is attached to water supply tube 111. Water then flows into cartridge 122 through ports 149 and passage 146 and moves out of cartridge 122 through passage 131 and ports 134. This substantially simplifies the installation of cartridge 122 into the water line adjacent the point of connection to the domestic or community water system.

Figure 16:
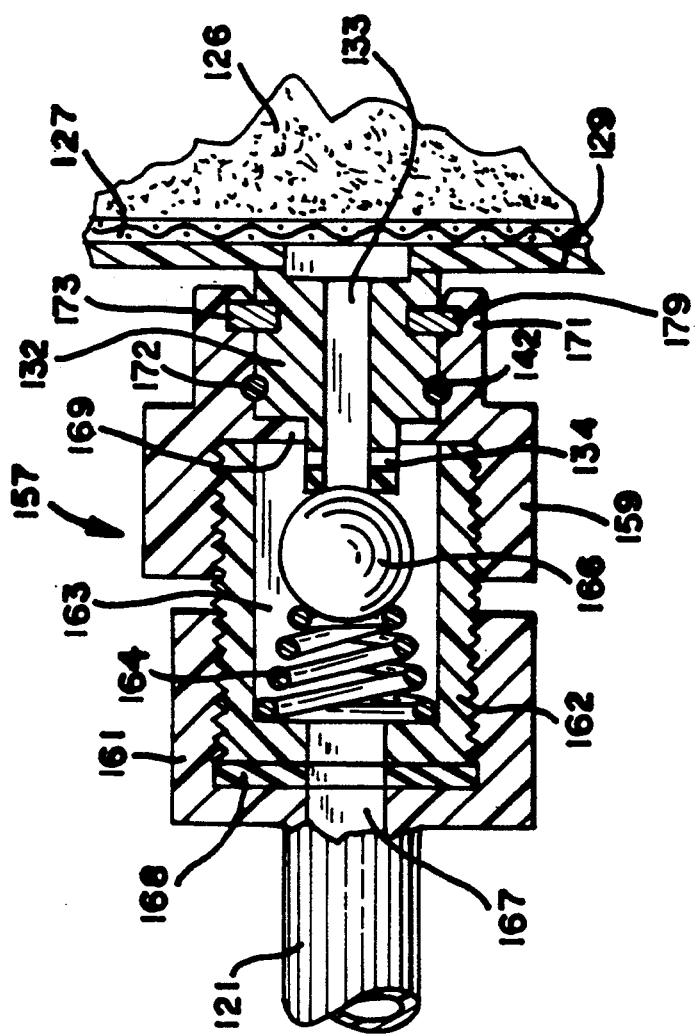
FIG. 16 is a sectional view taken along the line 16—16 of FIG. 10.

Referring to FIG. 16, connector 157 has a generally cylindrical body 162 that surrounds inner chamber 163. Connector body 162 has an outer threaded surface that cooperates with inner threaded surfaces of connector members 159 and 161 to hold members 159 and 161 on connector body 162. Connector members 159 and 161 are cup-shaped members having open tops. Members 159 and 161 are mounted on connector body 162 whereby their respective open tops are orientated toward each other. Connector member 161 is secured directly to the end of tube 121. An annular seal or washer 168 is located between connector body 162 and connector member 161 to eliminate water leakage from flow path 167. Each of the connector members 159 and 161 and the connector body 162 has a centrally located bottom opening to form a flow path 167 for water to move through chamber 163 and connector 157 and into cartridge 122. A spring 164 located in chamber 163 biases a ball or bead 166 into engagement with bottom wall 169 of connector member 159 to close the opening in wall 169 and block flow path 167. When reduced diameter end 143 of cartridge collar 132 is inserted through the opening in wall 169, bead 166 is moved away from wall 169 to open flow path 167 placing ports 134 inside chamber 163 of connector 157 and in communication with the passage of water source tube 121.

Connector member 159 has an annular flange 171 that receives and surrounds collar 132 of cartridge 122. Seal 142 fits into an annular groove 172 in flange 171 adjacent wall 169 to prevent leakage of water between connector 157 and cartridge 122. A groove 179 adjacent the outer end of connector flange 171 accommodates lever 173 that functions to releasably couple cartridge collar 132 to connector 157. Collar end 143 engages spring-biased bead 166 to hold bead 166 in the open position and allow water to flow into cartridge 122 for filtration through filter 126.

Figure 15:
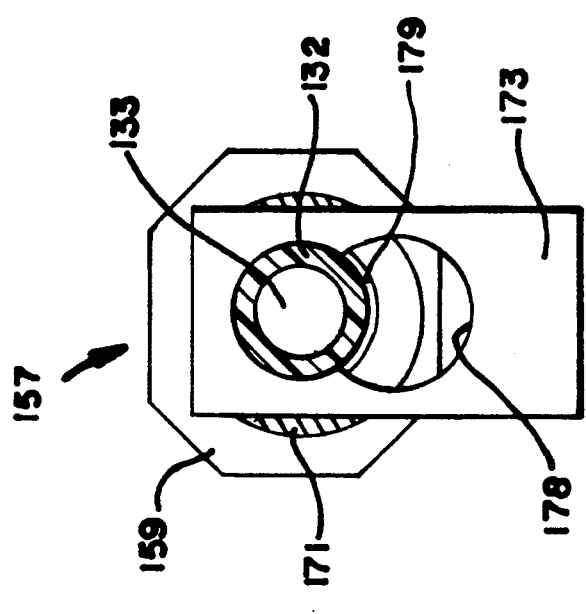
FIG. 15 is a sectional view taken along the line 15—15 of FIG. 10.

Referring to FIGS. 10 and 15, lever 173 is a generally rectangular-shaped plate slidably mounted in groove 179 of connector flange 171. The upper and lower ends of lever 173 are turned inwardly to form tabs or stops 176 and 177. The stops 176 and 177 engage connector flange 171 to limit vertical movement of lever 173 between coupled and uncoupled positions. As shown in FIG. 15, lever 173 has a center opening 178 having a smaller diameter top portion and a larger diameter bottom portion. Lever 173 is moved downwardly to position collar 132 in the top portion of opening 178 and releasably lock cartridge collar 132 to connector 157. The top portion of opening 178 encircles collar 132 and the top half of lever 173 fits into groove 136 of cartridge collar 132. The diameter of the top portion of opening 178 is substantially the same as the diameter of collar 132 at groove 136. When lever 173 is moved upwardly, the bottom portion of opening 178 is located adjacent and telescopes around collar 132 whereby the collar 132 can be unplugged and removed from connector 157. The outer diameter of cartridge collar 132 is less than the diameter of the bottom portion of opening 178 so that the collar 132 can be quickly and easily moved in and out of connector 157.

Connector 158 has substantially the same structure as connector 157. As shown in FIG. 9, connector 158 is secured directly to the end of water supply tube 111. Connector 158 has an annular flange that receives and surrounds collar 152 of cartridge 122. When reduced diameter section 156 of collar 152 is inserted into connector 158, a spring-biased valve, identical to bead valve 166 of connector 157, contained within connector 158 is moved to the open position whereby ports 149 are positioned inside the inner chamber of connector 158 and in communication with the passage of water supply tube 111. Connector 158 has a lever 174 slidably mounted for longitudinal movement relative to the lateral extension of connector 158. Lever 174 releasably couples cartridge collar 152 to connector 158 whereby purified water containing a residual disinfectant flows into tube 111 from cartridge 122.

Lever 174 is a generally rectangular-shaped plate having inwardly turned ends that engage the outer surface of connector 158 thereby limiting vertical movement of lever 174 between coupled and uncoupled positions. Lever 174 is moved downwardly into groove 151 of cartridge collar 152 to releasably lock cartridge collar 152 to connector 158 and tube 111. When lever 174 is moved upwardly, collar 152 can be unplugged and removed from connector 158.

In use, cartridge 120 is inserted between water supply tube 111 and water intake tube 113 that leads to dental instrument 100. Fittings 137 and 138 mounted on the ends of tubes 111 and 113 releasably lock opposite ends of cartridge 120 onto the ends of tubes 111 and 113. The disinfectant material contained within cartridge 120 purifies water flowing through the cartridge 120 adds residual disinfectant to the water supplied to dental instrument 100 and prevents back contamination beyond cartridge 120.

Cartridge 122 is inserted between water source tube 121 and water supply tube 111 adjacent the point of connection to a domestic or community purification system. Connectors 157 and 158 secured to the ends of tubes 121 and 111, respectively, releasably couple opposite ends 129 and 144 of cartridge 122 onto the ends of tubes 121 and 111. Plugging cartridge collars 132 and 152 into connectors 157 and 158 moves spring-biased valves 166 to the open position allowing water to flow through cartridge 122. Levers 173 and 174 are moved downwardly into grooves 136 and 151 of cartridge collars 132 and 152 to releasably lock the collars of cartridge 122 to connectors 157 and 158 and tubes 121 and 111. Disinfectant material 126 contained within cartridge chamber 124 neutralizes and kills disease causing bacteria, virus and other agents in the water as the water passes through cartridge 122 from water source tube 121. A residual disinfectant is eluted from disinfectant material 126 into the water at a constant predetermined rate to maintain a purified water condition. Cartridges 120 and 122 maintain a microbiologically pure water system for dental instrument 100 and prevent cross infection between dental patients and back flow of contamination to water supply system.

At the beginning of each work day cartridge 120 is removed from the water line and replaced with a new cartridge. Cartridge 122 is replaced on a less frequent basis which is determined by the cartridge size. Fittings 137 and 138 and connectors 157 and 158 provide quick and easy disconnection and connection of cartridges 120 and 122 to the water line. This ensures a continuous microbiologically pure water condition and provides for control of water contaminants that may be drawn back into the water system for dental instrument 100.

While there has been shown and described preferred embodiments of the water purification apparatus, it is understood that changes in materials and structures can be made by those skilled in the art without departing from the invention. The invention is defined in the following claims.

We claim:

1. A dental apparatus having a fluid supply system connected to a fluid source system comprising: a dental instrument having first tube means connected to the fluid source system, second tube means receiving fluid from the first tube means, third tube means receiving fluid from the second tube means, first fluid purification means releasably mounted on the first tube means and the second tube means, second fluid purification means releasably mounted on the second tube means opposite from the first fluid purification means and third tube means, the first and second fluid purification means each including filter means and a disinfectant means operable to filter, purify and supply disinfectant means to the fluid as the fluid passes through the disinfectant means, the disinfectant means remaining as a residual in the fluid as the fluid moves through the dental instrument and is discharged from the dental instrument to maintain a purified water condition within the fluid supply system for the dental instrument whereby when the fluid is discharged from the dental instrument the fluid is in a microbiologically pure condition and contains the disinfectant means, the disinfectant means neutralizing contaminants drawn back into the fluid supply system with the purification means preventing aspirated contaminants from traveling back beyond the purification means to prevent cross infection, first means connected to the first tube means and second tube means to releasably attach the first and second tube means, and second means connected to the second tube means and third tube means to releasably attach the second fluid purification means to the second and third tube means.

2. The apparatus of claim 1 wherein: the first and second fluid purification means each has chamber means, the disinfectant means located in the chamber means.

3. The apparatus of claim 1 wherein: the first and second fluid purification means each has coupling means located on outer ends thereof.

4. The apparatus of claim 1 wherein: the first and second fluid purification means each has filter means adjacent ends of the disinfectant means to retain the disinfectant means within the fluid purification means as fluid flows through the fluid purification means.

5. The apparatus of claim 1 wherein: the first and second fluid purification means each comprises a cartridge having a housing defining a chamber, the housing having opposite ends, each end having a passage open to the chamber, the filter means and disinfectant means located in the chamber.

6. The apparatus of claim 1 wherein: the first fluid purification means includes collar means having groove means open to an outer surface of the collar means, the groove means cooperating with the first means to releasably couple the first fluid purification means to the first and second tube means.

7. The apparatus of claim 1 wherein: the second fluid purification means includes collar means cooperating with the second means to releasably attach the second fluid purification means to the second and third tube means.

8. The apparatus of claim 1 wherein: the disinfectant means is an iodinated anionic exchange resin.

9. The apparatus of claim 1 wherein: the disinfectant means is a resin containing a continuous, fix-rate release iodinated resin $I_{(n)}$.

10. The apparatus of claim 1 wherein: the disinfectant means is a specified and consistent amount of iodine released from the disinfectant means into the fluid as the fluid passes through the disinfectant means so as to kill microbial contaminants or prevent cell reproduction rendering the contaminants harmless.

11. The apparatus of claim 1 wherein: the first fluid purification means is located adjacent a point of connection of the fluid supply system to the fluid source system, and the second fluid purification means being located adjacent a point of connection of the fluid supply system to the dental instrument.

12. A dual cartridge apparatus located in a water line connected to a water source system and leading to a dental instrument having a water supply system comprising: a first cartridge releasably coupled to the water line adjacent a point of connection of the water line to the water source system, the first cartridge having a housing defining an internal chamber, disinfectant means located in the chamber operable to purify and release a disinfectant into the water flowing through the chamber, the disinfectant remaining as a residual in the water as the water moves into the water line away from the first cartridge to kill microbial contaminants or prevent cell reproduction rendering the contaminants harmless, a second cartridge releasably coupled to the water line adjacent a point of connection of the water line to the dental instrument, the second cartridge having a housing defining an internal chamber, disinfectant means located in the chamber operable to purify and release a disinfectant into water flowing through the chamber, the disinfectant remaining as a residual in the water as the water moves between the second cartridge and the dental instrument whereby when the water is discharged from the dental instrument the water is in a microbiologically pure condition and contains the disinfectant, the disinfectant neutralizing contaminants drawn back into the water supply system to prevent cross infection.

13. The apparatus of claim 12 wherein: the first and second cartridges each has filter means located in the chamber adjacent ends of the disinfectant means to filter the water and disinfectant means in the chamber and allow water to flow through the chamber.

14. The apparatus of claim 12 wherein: the housing of each of the first and second cartridges has opposite ends, each end having a passage open to the chamber, and coupling means located adjacent the passage.

15. The apparatus of claim 14 including: filter means adjacent ends of the disinfectant means and passages, each passage having a diameter less than a diameter of the porous means.

16. The apparatus of claim 12 wherein: the first cartridge has coupling means comprising a pair of generally tubular collars extending from opposing ends of the housing, each collar having an annular groove open to the outer surface of the collar cooperating with releasable connector means to releasably couple the first cartridge to the water line adjacent the point of connection of the water line to the water source system.

17. The apparatus of claim 12 wherein: the second cartridge has coupling means comprising a pair of tubular collars attached to opposite ends of the housing, each collar having a threaded outer surface to releasably connect the cartridge to the water line adjacent the point of connection of the water line to the dental instrument.

18. The apparatus of claim 12 wherein: the disinfectant means of each of the first and second cartridges comprises an iodinated anionic exchange resin.

19. The apparatus of claim 12 wherein: the disinfectant means of each of the first and second cartridges is a resin containing a continuous, fix-rate release iodinated resin $I_{(n)}$.

20. The apparatus of claim 12 wherein: the disinfectant of each of the first and second cartridges comprises a specified and consistent amount of iodine released from the disinfectant means into the water as the water passes through the disinfectant means so as to kill microbial contaminants or prevent cell reproduction rendering the contaminants harmless.

21. A dual cartridge apparatus for purifying water originating from a water source system and supplied through a water supply system to a dental instrument comprising: a first cartridge located in the water supply system adjacent the water source system, first coupling means releasably connecting the first cartridge adjacent the water source system, a second cartridge located in the water supply system adjacent the dental instrument distal from the first cartridge, and second coupling means releasably connecting the second cartridge adjacent the dental instrument, the first and second cartridges each having a housing defining an internal chamber, the housing having opposite ends, each end having a passage open to the chamber, disinfectant means located in the chamber operable to purify and release disinfectant means into water flowing through the disinfectant means, filter means located in the chamber adjacent ends of the disinfectant means to filter the water and retain the disinfectant means in the chamber and allow water to flow through the chamber.

22. The apparatus of claim 21 wherein: the disinfectant means comprises an iodinated anionic exchange resin.

23. The apparatus of claim 21 wherein: the disinfectant means is a resin containing a continuous, fix-rate release iodinated resin $I_{(n)}$.

24. The apparatus of claim 21 wherein: the disinfectant means is a biocidal continuous fixed-rate release iodinated resin.

25. The apparatus of claim 21 wherein: the disinfectant means is a specified and consistent amount of iodine released from the disinfectant means into the water as the water passes through the disinfectant means so as to kill microbial contaminants or prevent cell reproduction rendering the contaminants harmless and remaining as a residual in the water as the water moves between the first cartridge and the dental instrument whereby when the water is discharged from the dental instrument the water contains the residual iodine to neutralize contaminants drawn back into the water supply system and prevent cross infection.

* * * * *